United States Patent
Mehta

(10) Patent No.: US 10,863,815 B2
(45) Date of Patent: Dec. 15, 2020

(54) DISPOSABLE SINGLE USE APPLICATOR ASSEMBLY WITH A CHEMICAL COMPOSITION

(71) Applicant: JE MATADI, INC., Stafford, TX (US)

(72) Inventor: Pershant Mehta, Stafford, TX (US)

(73) Assignee: Je Matadi, Inc., Stafford, TX (US)

( * ) Notice: Subject to any disclaimer, the term of this patent is extended or adjusted under 35 U.S.C. 154(b) by 9 days.

(21) Appl. No.: 15/874,107

(22) Filed: Jan. 18, 2018

(65) Prior Publication Data

US 2018/0199694 A1   Jul. 19, 2018

Related U.S. Application Data

(60) Provisional application No. 62/447,835, filed on Jan. 18, 2017.

(51) Int. Cl.
| | |
|---|---|
| *A45D 40/26* | (2006.01) |
| *A45D 37/00* | (2006.01) |
| *A45D 40/00* | (2006.01) |
| *A61Q 19/00* | (2006.01) |
| *A61K 8/04* | (2006.01) |

(52) U.S. Cl.
CPC .......... *A45D 40/262* (2013.01); *A45D 37/00* (2013.01); *A45D 40/0087* (2013.01); *A61K 8/046* (2013.01); *A61Q 19/00* (2013.01); *A45D 2200/1009* (2013.01); *A45D 2200/1036* (2013.01); *A61K 2800/87* (2013.01)

(58) Field of Classification Search
CPC ............................ A45D 40/0087; A45D 37/00
See application file for complete search history.

(56) References Cited

U.S. PATENT DOCUMENTS

| | | | | |
|---|---|---|---|---|
| 1,791,351 | A | | 2/1931 | Chase |
| 1,888,314 | A | | 11/1932 | Framke |
| 2,557,141 | A | * | 6/1951 | Rebora .................. A45D 40/22 132/294 |
| 2,598,323 | A | | 5/1952 | Wagar |
| 4,884,719 | A | * | 12/1989 | Levine .................. A45D 33/00 221/25 |
| 5,647,941 | A | | 7/1997 | Gunderman et al. |
| 6,062,234 | A | * | 5/2000 | Finocchiaro .......... A45D 33/00 132/294 |

(Continued)

FOREIGN PATENT DOCUMENTS

| | | |
|---|---|---|
| JP | 04187627 | 11/1990 |
| WO | 2005027684 | 3/2005 |

*Primary Examiner* — David P Angwin
*Assistant Examiner* — Bradley S Oliver
(74) *Attorney, Agent, or Firm* — Craft Chu PLLC; Andrew W. Chu

(57) ABSTRACT

The applicator assembly delivers a cosmetic, health, or hygiene chemical composition in an active state to the user for a disposable single use. The applicator assembly includes a wrapper, and an insert. The insert holds the chemical composition, and the insert is made of a foam composition compatible with the chemical composition. The system and method for manufacturing the assembly is a web conversion process for the chemical composition and foam composition of the assembly. The applicator assembly includes the wrapper formed by a top sheet and a bottom sheet, and an insert formed by an insert body with a handle portion and an applicator portion and the chemical composition.

7 Claims, 7 Drawing Sheets

(56) References Cited

U.S. PATENT DOCUMENTS

| | | | |
|---|---|---|---|
| 6,190,730 B1 | 2/2001 | Matsos | |
| 6,260,887 B1 | 7/2001 | Fujii | |
| 6,312,181 B1 | 11/2001 | Joulia | |
| 6,451,397 B1* | 9/2002 | Hagen | A45D 40/0087 206/484 |
| 6,772,884 B2* | 8/2004 | Mathiez | A45D 40/0087 206/581 |
| 7,297,285 B2 | 11/2007 | Chang | |
| 7,514,071 B2 | 4/2009 | Simon | |
| 8,087,417 B2* | 1/2012 | Dobler | A45D 40/0087 132/320 |
| 8,814,455 B2* | 8/2014 | Golden | A45D 40/0087 401/132 |
| 9,113,692 B2* | 8/2015 | Khan | A45D 40/00 |
| 9,301,589 B2 | 4/2016 | Griffiths et al. | |
| 2003/0004089 A1* | 1/2003 | Huber | A45D 40/0087 512/1 |
| 2006/0233847 A1* | 10/2006 | Mammone | A45D 33/38 424/401 |
| 2007/0130708 A1* | 6/2007 | Powley | A45D 34/02 15/104.94 |
| 2008/0002282 A1 | 1/2008 | Henrik | |
| 2008/0002286 A1 | 1/2008 | Frank et al. | |
| 2008/0002302 A1 | 1/2008 | Burtzlaff et al. | |
| 2008/0011319 A1* | 1/2008 | Ripoli | A45D 40/0087 132/286 |
| 2014/0019503 A1 | 7/2014 | Balleis et al. | |

* cited by examiner

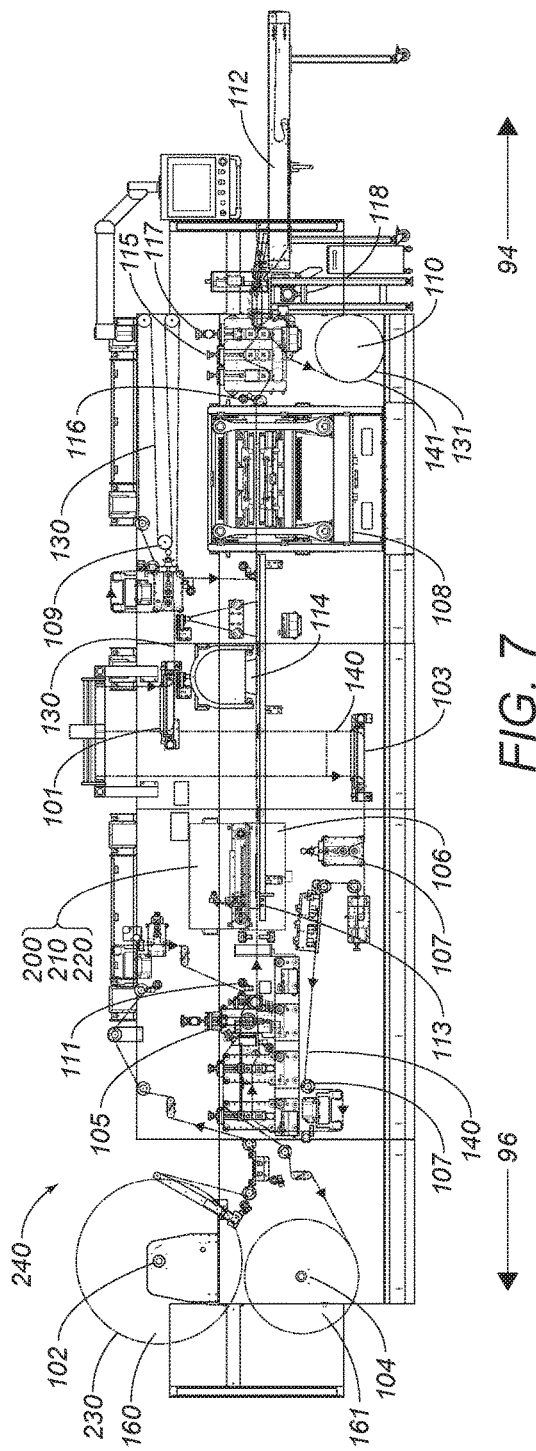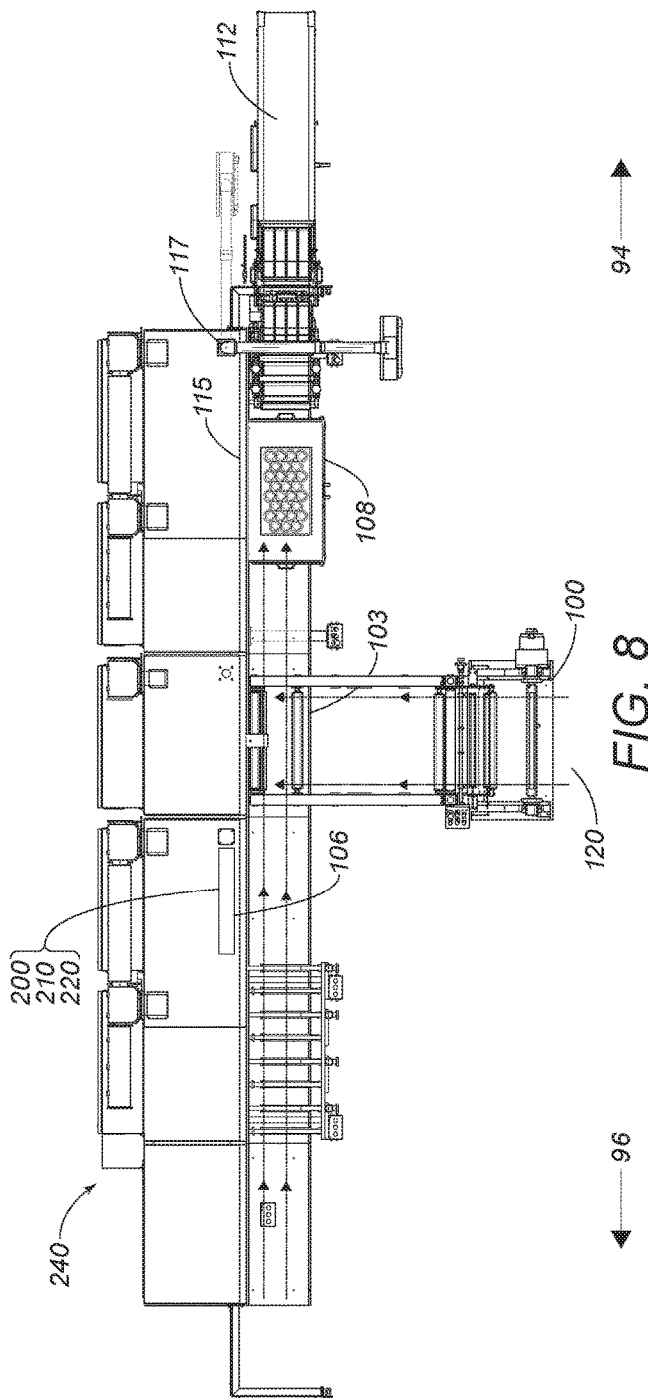

DISPOSABLE SINGLE USE APPLICATOR ASSEMBLY WITH A CHEMICAL COMPOSITION

CROSS-REFERENCE TO RELATED APPLICATIONS

See Application Data Sheet.

STATEMENT REGARDING FEDERALLY SPONSORED RESEARCH OR DEVELOPMENT

Not applicable.

THE NAMES OF PARTIES TO A JOINT RESEARCH AGREEMENT

Not applicable.

INCORPORATION-BY-REFERENCE OF MATERIAL SUBMITTED ON A COMPACT DISC OR AS A TEXT FILE VIA THE OFFICE ELECTRONIC FILING SYSTEM (EFS-WEB)

Not applicable.

STATEMENT REGARDING PRIOR DISCLOSURES BY THE INVENTOR OR A JOINT INVENTOR

Not applicable.

BACKGROUND OF THE INVENTION

1. Field of the Invention

The present invention relates to cosmetics, health, and hygiene products to be packaged for disposable single use. More particularly, the present invention relates to disposable single use applicator assemblies with a chemical composition. The present invention also relates to the chemical composition in the assembly and the foam composition forming the applicator of the assembly. The present invention further relates to the system and method for manufacturing the disposable single use applicator assembly.

2. Description of Related Art Including Information Disclosed Under 37 CFR 1.97 and 37 CFR 1.98

Various industries have developed systems and methods for disposable single use packets. The toiletry appliance of U.S. Pat. No. 1,791,351, issued to Chase on 3 Feb. 1931, and the make-up applicator of U.S. Pat. No. 1,888,314, issued to Framke on 22 Nov. 1932, are two early examples in the hygiene and cosmetics fields. U.S. Pat. No. 2,598,323, issued to Wagar on 27 May 1952, is an early example of an embossing machine to manufacture disposable single use packets.

More recent patents cover developments in the material selection of disposable single use packets. U.S. Pat. No. 6,062,234, issued to Finocchiaro et al on 16 May 2000, and U.S. Pat. No. 6,312,181, issued to Joulia on 6 Nov. 2001, disclose disposable single use packets formed of particular materials. U.S. Pat. No. 7,514,071, issued to Simon on 7 Apr. 2009, and U.S. Pat. No. 8,087,417, issued to Dobler et al on 3 Jan. 2012, describe substrates selected for the adhering different cosmetic chemical compositions in a disposable single use packet. U.S. Pat. No. 9,113,692, issued to Khan et al on 25 Aug. 2015, and U.S. Pat. No. 9,301,589, issued to Griffiths et al on 5 Apr. 2016, disclose specifics for the material selection of the chemical composition and the substrate.

Furthermore, several patents and publications relate to the development of methods for assembling disposable single use packets.

U.S. Pat. No. 5,647,941, issued to Gunderman et al on 15 Jul. 1997, discloses a method for making a lipstick sampler, and U.S. Pat. No. 6,190,730, issued to Matsos on 20 Feb. 2001, describes another method by the same group of inventors for U.S. Pat. No. 5,647,941, which includes cosmetics besides lipstick. U.S. Pat. No. 6,260,887, issued to Fujii on 17 Jul. 2001, and U.S. Pat. No. 7,297,285, issued to Chang on 20 Nov. 2007, disclose embossing methods for adhering chemical compositions on a substrate, which can be adapted for disposable single use packets. U.S. Patent No. 2008/0022866, published for Frank et al on 31 Jan. 2008, and U.S. Patent No. 2008/0022821, published for Henrik on 31 Jan. 2008 both disclose the manufacturing machine for assembling disposable single use packets. More recently, U.S. Patent No. 2014/0195038, published for Balleis et al on 10 Jul. 2014, describe aspects of a web conversion feature in the overall manufacturing process.

It is an object of the present invention to provide a disposable single use applicator assembly with a chemical composition.

It is another object of the present invention to provide a disposable single use applicator assembly compatible with a web conversion manufacturing process.

It is still another object of the present invention to provide a disposable single use applicator assembly with a cosmetic, health or hygiene chemical composition and an applicator with a chemical composition for delivery of the cosmetic, health, or hygiene chemical composition in an active state to the user.

It is still another object of the present invention to provide a disposable single use applicator assembly with components that maintain alignment during the manufacturing process before sealing.

It is another object of the present invention to provide an embodiment of an applicator assembly to store a limited amount of a cosmetic.

It is still another object of the present invention to provide an embodiment of an applicator assembly to store an amount of a cosmetic for a single application of the cosmetic.

It is yet another object of the present invention to provide an embodiment of an applicator assembly to store a limited amount of a cosmetic in a disposable and portable container.

It is another object of the present invention to provide an applicator assembly to store and carry cosmetics in a simple, easy, and inexpensive container.

It is an object of the present invention to provide a chemical composition for a disposable single use applicator assembly.

It is another object of the present invention to provide a chemical composition compatible with a web conversion manufacturing process for a disposable single use applicator assembly.

It is still another object of the present invention to provide a chemical composition that adheres to an applicator during the manufacturing process so as to maintain alignment before sealing.

It is still another object of the present invention to provide a chemical composition that dries during the manufacturing process before sealing.

It is an object of the present invention to provide a foam composition for an applicator or insert of a disposable single use applicator assembly.

It is another object of the present invention to provide a foam composition compatible with a web conversion manufacturing process for a disposable single use applicator assembly.

It is still another object of the present invention to foam composition that can adheres a chemical composition during the manufacturing process before sealing.

It is still another object of the present invention to provide a foam composition that maintains alignment during the manufacturing process before sealing.

It is an object of the present invention to provide a disposable single use applicator and packaging assembly.

It is an object of the present invention to provide a system and method for manufacturing a disposable single use applicator assembly.

It is another object of the present invention to provide a web conversion method of manufacturing a disposable single use applicator assembly.

It is another object of the present invention to provide a system to perform the web conversion method of manufacturing a disposable single use applicator assembly.

It is still another object of the present invention to provide a system and method of manufacturing a disposable single use applicator assembly for delivery of the cosmetic, health, or hygiene chemical composition in an active state to the user.

It is still another object of the present invention to provide a system and method of manufacturing a disposable single use applicator assembly maintaining alignment during the web conversion of the manufacturing process.

These and other objectives and advantages of the present invention will become apparent from a reading of the attached specifications and appended claims.

BRIEF SUMMARY OF THE INVENTION

Embodiments of the present invention include the applicator assembly to deliver a chemical composition in an active state for a disposable single use. The chemical composition can be cosmetics or a medical or hygiene related substance. The assembly includes an applicator for supporting the chemical composition during manufacturing, storage in the assembly, and administering the chemical composition. The assembly includes a wrapper and an insert. The insert holds the chemical composition, and the insert is made of a foam composition compatible with the chemical composition. The system and method for manufacturing the assembly is a web conversion process for the chemical composition and foam composition of the assembly.

The present invention includes the applicator assembly itself. The applicator assembly stores and transports the chemical composition. The assembly includes the wrapper formed by a top sheet and a bottom sheet, and the insert is formed by an insert body with a handle portion and an applicator portion and the chemical composition. Embodiments of the applicator assembly include a border to seal the insert in the wrapper and an incision to form a tab to open the assembly. Additionally, the insert body and the border have features to set and maintain the position of the insert within the wrapper for stable and reliable storage in the assembly. The method of manufacturing the applicator assembly is also included as another embodiment.

BRIEF DESCRIPTION OF THE SEVERAL VIEWS OF THE DRAWINGS

FIG. 7 is a side elevation view of a system to manufacture an assembly, according to an embodiment of the present invention.

FIG. 8 is a top plan view of the system to manufacture an assembly, according to FIG. 7.

DETAILED DESCRIPTION OF THE INVENTION

Figure 1:
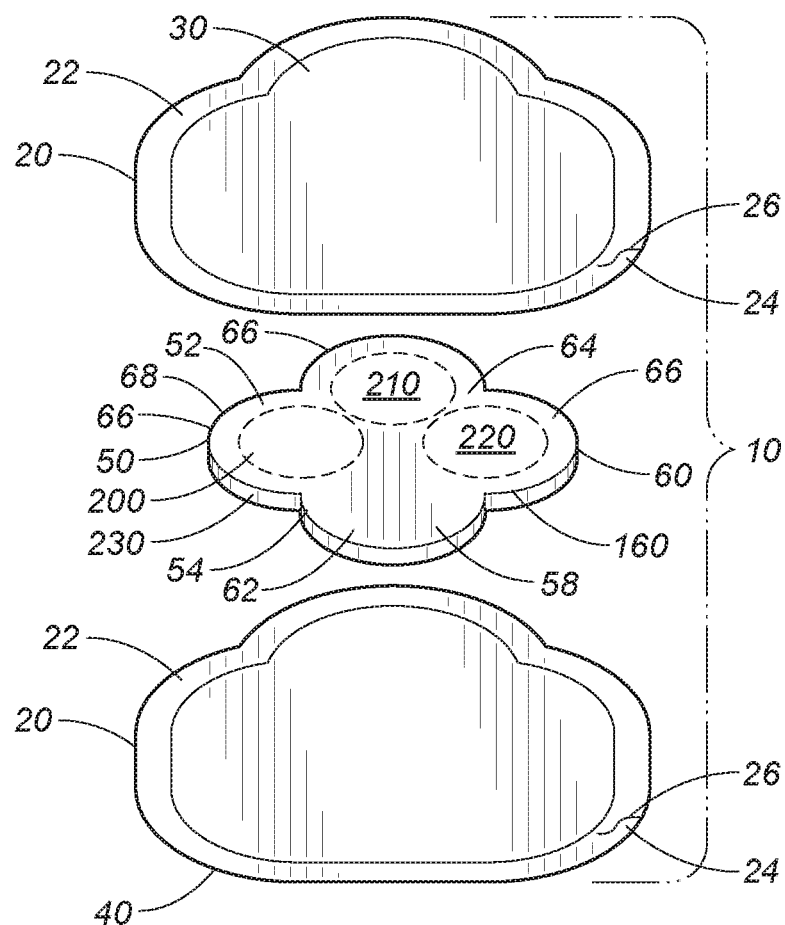
FIG. 1 is an exploded perspective view of an embodiment of an assembly for storing and transporting a chemical composition, according to the present invention.

The overall present invention includes the disposable single use applicator assembly, the chemical composition for the assembly, and the foam composition for the assembly with the chemical composition. The system to manufacture the assembly, and the method for manufacturing with the system are also included as embodiments.

Disposable Single use Applicator Assembly with a Chemical Composition

Embodiments of the present invention include the assembly 10 of FIGS. 1-6 and 10-12. The assembly 10 stores and transports a chemical composition 200, 210, 220. A set amount of the chemical composition 200, 210, 220, corresponding to a single dose of medication or single application of a cosmetic, is packaged on an applicator within the assembly 10. The medication can be an ointment or antiseptic, or other topical treatments. The cosmetic can include a face, skin, eye, or other beauty effect, and multiple cosmetics can be stored and transported in the assembly. Chemical compositions 200, 210, 220 can have any combination of being the same or different from each other. Two or three different chemical combinations are possible, such as chemical composition 200 and chemical composition 210 being foundation, and chemical composition 220 being bronzer. The assembly 10 provides convenience and versatility.

Figure 2:
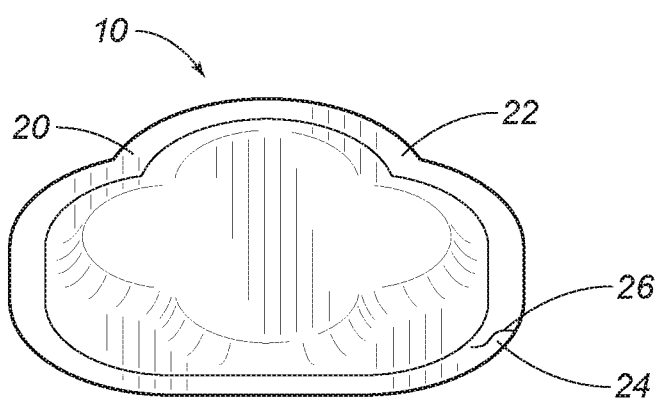
FIG. 2 is an upper perspective view of the packaged configuration of the assembly, according to an embodiment of the present invention.
Figure 3:
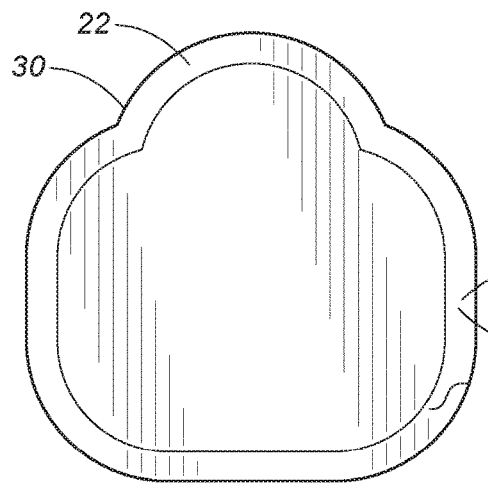
FIG. 3 is a front elevation view of a top sheet of the assembly, according to an embodiment of the present invention.
Figure 4:
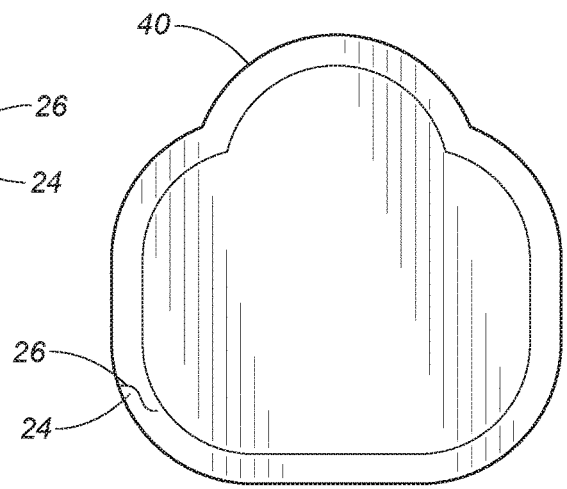
FIG. 4 is a front elevation view of a bottom sheet of the assembly, according to an embodiment of the present invention.
Figure 5:
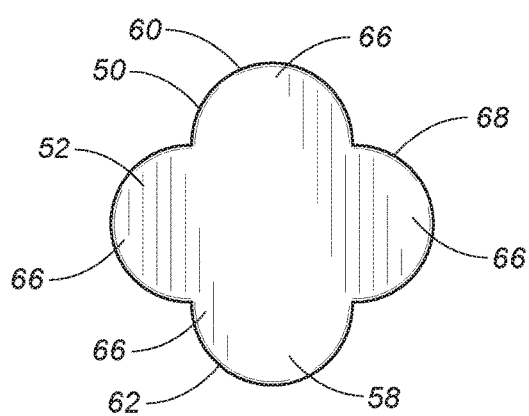
FIG. 5 is a front elevation view of an insert of the assembly, according to an embodiment of the present invention.
Figure 6:
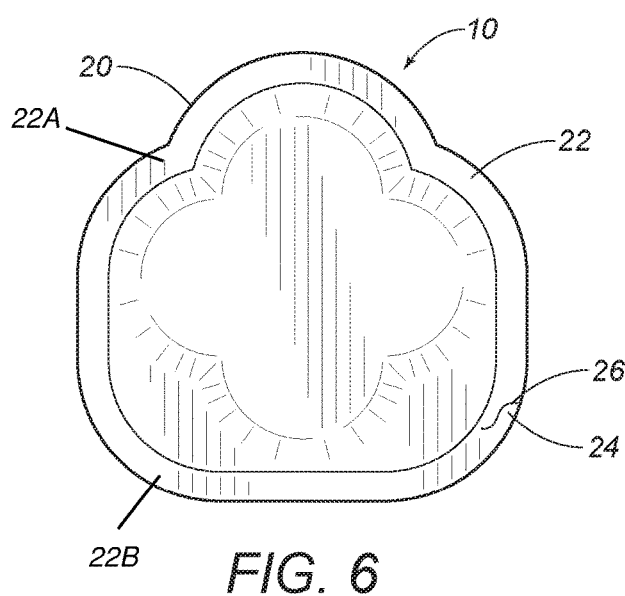
FIG. 6 is a front elevation view of the packaged configuration of FIG. 2.

According the FIGS. 1-6, the assembly 10 includes a wrapper 20 having a top sheet 30 and a bottom sheet 40, and an insert 50 having a top surface 52 and a bottom surface 54. FIG. 1 shows an exploded view, while FIGS. 2 and 6 show a packaged configuration. The insert 50 is comprised of an insert body 60 with a handle portion 62 and an applicator portion 64, as also seen in FIG. 5 without the chemical composition 200, 210, 220. The top sheet 30 of FIG. 3 is sealed to the bottom sheet 40 of FIG. 4 as shown in FIG. 1. The top sheet 30 and the bottom sheet 40 form a border 22 along a perimeter of the top sheet 30 and the bottom sheet 40. The insert 50 being positioned between the top sheet 30 and the bottom sheet 40. FIGS. 1-6 show the border 22 aligned with the applicator portion 64 only so as to maintain the insert 50 in place within the wrapper 20.

In some embodiments, the assembly 10 includes a tab 24 being comprised of an incision 26 in the border 22. The incision 26 is within the border 22 so that the insert 50 remains sealed within the assembly 10 and the border 22. The tab 24 can be used to separate the top sheet 30 and the bottom sheet 40. The tab 24 tears the border 22, so that the top sheet 30 and bottom sheet 40 no longer seal the insert 50 in the assembly 10.

FIG. 5 shows an embodiment of the insert body 60 having rotational symmetry of having at least four cyclic groups 66. In this front elevation view, the clover shape has four cyclic groups, but other embodiments may have different rotational symmetry. In the present invention, the handle portion 62 corresponds to only one cyclic group 66. FIG. 6 shows the border 22 being comprised of an applicator border segment 22A and a handle border segment 22B. The border 22 is aligned with the applicator portion 64 only so as to maintain the insert 50 in place within the wrapper 20, such that the border 22 is aligned with the cyclic groups 66 corresponding to the applicator portion 64. The applicator border segment 22A is aligned with the cyclic groups 66 corresponding to the applicator portion 64 and the set amount 200, 210, 220 on at least one cyclic group 66 corresponding to the application portion 64 and directly opposite the handle portion 62. The handle border segment 22B extends across the insert 50 adjacent to the handle portion 62. In some embodiments, the border can be aligned with cyclic groups 66 corresponding to the application portion 64 directly opposite the handle portion 62. Alternatively, the border 22 may align with at least one cyclic group 66 corresponding to the application portion 64 and directly opposite the handle portion 62. In still another embodiment, the border 22 aligns with parts of cyclic groups 66 corresponding to the application portion 64 corresponding to a side 68 of the insert body 60 opposite to the handle portion 62, as in FIG. 1.

When the insert 50 is separated from the assembly 10 for use, the handle portion 62 is accessible on the top surface 52 and on the bottom surface 54. The bottom surface 54 can be smooth, and the top surface 52 can be identical to the bottom surface 54 or different with a different texture for holding the chemical composition 200, 210, 220. Alternatively, the handle portion 62 can further comprise a gripping means 58, such as a pad, indentation, or tacky element. The gripping means 58 is sufficient for gripping by the user. FIG. 1 shows the gripping means 58 as a smooth surface.

FIG. 1 shows the embodiment of the insert 50 further comprising: a set amount of a chemical composition 200, 210, 220, corresponding to a single dose or single application. The set amount is positioned on the applicator portion 64. When the insert body 60 has rotational symmetry having at least four cyclic groups 66, the handle portion 62 corresponds to only one cyclic group 66, and the set amount of chemical composition 200, 210, 220 is divided between each cyclic group 66 of the applicator portion 64. Each cyclic group of the applicator portion having a respective set amount portion. There are embodiments with the set amount corresponds to a plurality of set amounts, such as a plurality of different cosmetics for a single application. In this embodiment, the chemical composition is a plurality of chemical compositions 200, 210, 220, and when the insert body 60 has rotational symmetry of at least four cyclic groups 66, each set amount of each chemical composition 200, 210, 220 is positioned on a corresponding cyclic group 66 of the applicator portion 64. Each cosmetic is positioned on a respective cyclic group 66 of the applicator portion 64 separate from other cosmetics.

Chemical Composition for a Disposable Single use Applicator Assembly

Embodiments of the chemical composition 200, 210, 220 are shown in FIG. 1. As a medication or cosmetic, the chemical composition 200, 210, 220 of the present invention must be compatible with the insert body 60 and suitable for disposable single use storage and transport. Not all chemical compositions will remain active and viable, under the conditions in the assembly 10 or under the conditions for manufacturing the assembly 10. In the field of cosmetics, the chemical composition must retain consistency for reliable application and color for the proper makeup effect. The vibrancy of the makeup effect can be achieved under the conditions in the assembly 10 and under the conditions for manufacturing the assembly 10.

The present invention includes a chemical composition 200, 210, 220 comprising 55-70 weight percent of amorphous silica, 4-12 weight percent of a white adhesive agent, 1-30 weight percent of a coloring agent, and 0.5-4.0 weight percent a first aromatic preservative agent. The amorphous silica is an absorbing agent and a thickening agent. The white adhesive agent can be magnesium myristate in some embodiments. In the present invention, the white adhesive agent allows for storage in the assembly 10 and adhesion to the insert body 60 without affecting color. Although some adhesive agents can have color, the present invention achieves the desired vibrancy of color without a colored adhesive agent. The coloring agent can be iron oxides, which have the known feature of coloring cosmetics. However, the chemical compositions 200, 210, 220 to have level of color adhered to the insert body 60, sealed in a wrapper 20 and manufactured by the system 240 in FIGS. 7-12 are embodiments of the present invention. The first aromatic preservative agent can be comprised of a vegetable based essential oil fraction. The scent and activity of the chemical composition are set for consistency under the conditions of the assembly 10.

In some embodiments, the chemical composition 200, 210, 220 further comprises equal to or less than 5 weight percent of a sealing agent, such as phenyl trimethicone. The sealing agent can be based on silica to be compatible in the chemical composition 200, 210, 220. The sealing agent sets viscosity and prevents foaming, which relates to storage conditions on the insert body 60.

The chemical composition can be further comprised of equal to or less than 1 weight percent of a preservative agent. In addition to the first aromatic preservative agent, another preservative agent can be added to prevent development of microorganisms. Again, in the sequence of manufacturing, the chemical composition 200, 210, 220 can be exposed to air with microorganisms. In some embodiments, this other preservative agent is Potassium sorbate.

The chemical composition can also be comprised of equal to or less than 2 weight percent of a second aromatic preservative agent. Just as there can be additional preservative agent, there can also be a second aromatic preservative agent. The chemical composition 200, 210, 220 finds the synergy of vegetable based first aromatic preservative agent with another preservative agent and the second aromatic preservative agent, such as phenoxyethanol. The redundancy is beyond the prior art and allows the chemical composition 200, 210, 220 to be contained in the assembly 10.

Embodiments of the chemical composition also include equal to or less than 20 weight percent of a bulking agent, such as synthetic fluorophlogopite. The bulking agent adjusts viscosity and can support the amorphous silica as the thickening agent. The range and overlap of redundancy sets the chemical composition 200, 210, 220 beyond the prior art disclosures of these chemical compounds in isolation. Although balancing any chemical composition for a desired effect is known, the present invention selects redundancies in particular ranges and overlap for the desired effect in an innovative combination related to the assembly 10 and manufacture of the assembly 10. The chemical composition 200, 210, 220 is an embodiment of the present invention.

Figure 10:
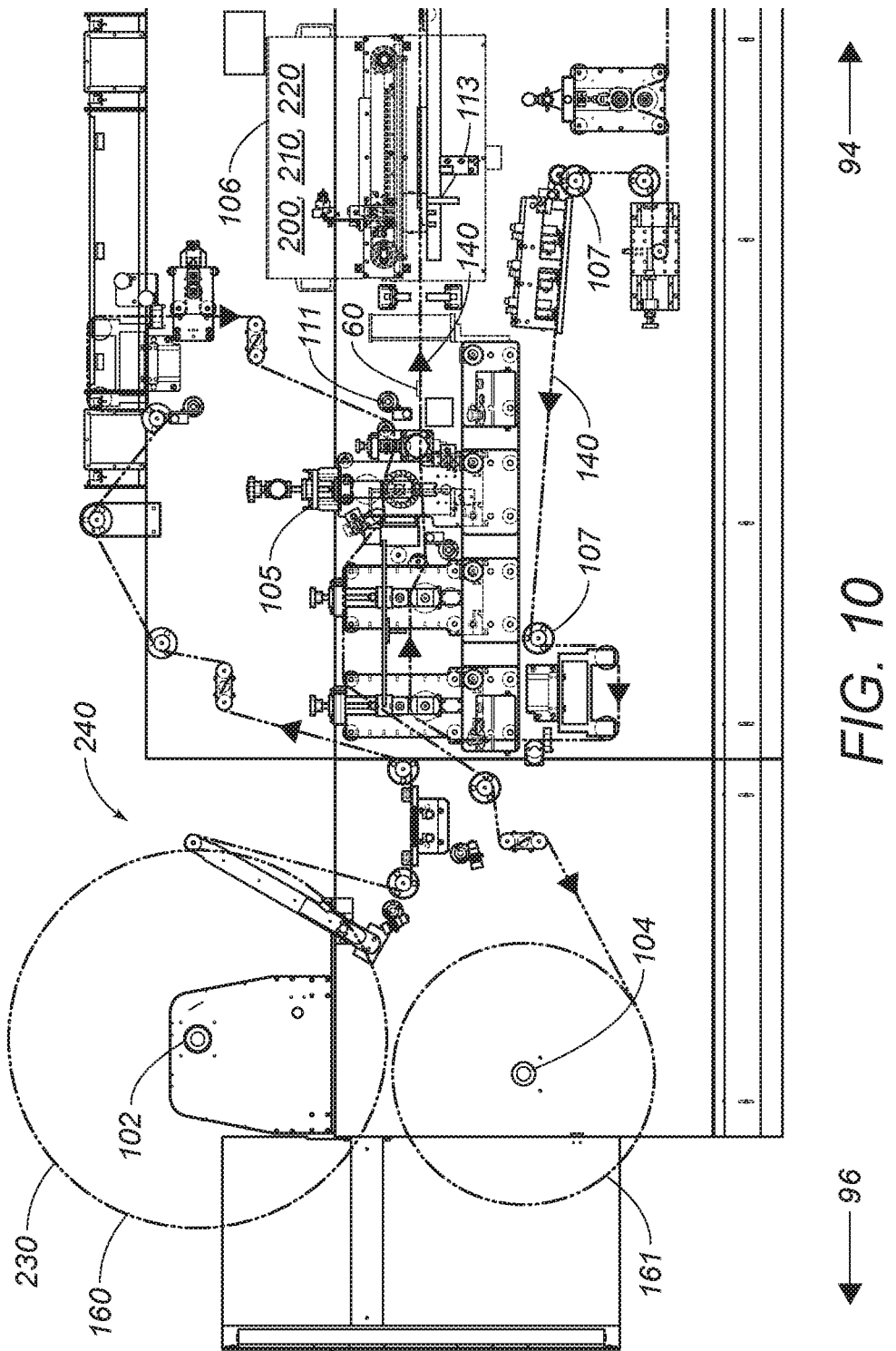
FIG. 10 is an enlarged side elevation view of a portion of a system to manufacture an assembly, according to an embodiment of the present invention.

Foam Composition for a Disposable Single use Applicator Assembly with a Chemical Composition Embodiments of the foam material 160 are shown in FIGS. 1, 7 and 10. The insert body 60 is formed by the foam material 160. The foam material is comprised of a foam composition 230. Similar to the chemical composition 200, 210, 220, the insert body 60 is comprised of a foam composition 230 suitable for disposable single use storage and transport. Not all foam compositions will support the chemical compositions 200, 210, 200 as active and viable, under the conditions in the assembly 10 or under the conditions for manufacturing the assembly 10. In the field of cosmetics, the foam composition must have durability, hardness, and absorbency to be used in a manufacturing process and hold a chemical composition. In the present invention, the foam composition 230 must have the compatibility with the chemical composition 200, 210, 220 of the assembly 10 during manufacturing and storage so as to retain consistency for reliable application and activity for the proper makeup effect.

The present invention includes a foam composition 230 comprising a reaction product of water, clay, polyacrylate, silane, methanol, ethylenediamine, and polyurethane prepolymer. The foam composition 230 is hydrophilic so that the absorption of the chemical composition 200, 210, 220 is limited. The foam composition 230 has a melting point greater than 350 F and a specific gravity of 0.3 to 0.5 for the durability and hardness suitable for the assembly 10 and manufacture of the assembly 10. The embodiments of the polyurethane foam of the present invention is compatible with the range and overlap of redundancy in the chemical composition 200, 210, 220 beyond the prior art disclosures of water, clay, polyacrylate, silane, methanol, ethylenediamine, and polyurethane prepolymer in isolation. Although any foam composition can be developed for desired durability, hardness, and absorbency, the present invention selects a reaction product in combination with particular ranges and overlap of a chemical composition 200, 210, 220 in the assembly 10. The foam composition 230 is another embodiment of the present invention.

System to Manufacture a Disposable Single use Applicator Assembly with a Chemical Composition Embodiments of the present invention include the system 240 for manufacturing the assembly 10 of FIGS. 1-6 and 10-12. The system 240 is shown in FIGS. 7-12 as a web conversion device. The assembly 10 is formed from rolls of material, top sheet material 130, bottom sheet material 140, and foam material 160, and there are cutting, sealing, and conveying steps producing the web materials as a perforated top material sheet 131, a perforated bottom material sheet 141, and perforated foam material sheet 161 to be tracked on course through the system 240. Additionally, there is the chemical composition 200, 210, 220 to be inserted into the system 240 for dispensing, curing, and sealing in coordination with the regular web conversion steps. The system 240 of the present invention elevates a web conversion device for a disposable single use applicator assembly with a chemical composition.

Figure 9:
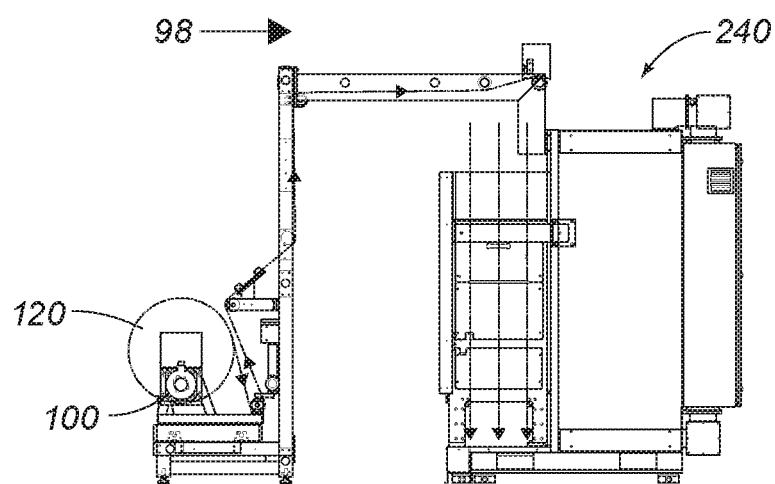
FIG. 9 is an end elevation view of the system to manufacture an assembly, according to FIG. 7.

FIGS. 7-9 show the system 240 for manufacturing the assembly 10, comprising a first roll 100 of wrapper material 120 mounted in a first direction 98. The first roll 100 dispenses the wrapper material 120 in the first direction 98 in FIG. 9. The wrapper material 120 splits into a top sheet material 130 and a bottom sheet material 140 in FIGS. 7 and 10. The split of the wrapper material 120 enables the assembly 10 to be aligned according to distance. The coordination and matching of markings for each assembly 10 on the top sheet material 130 and bottom sheet material 140 only need to travel the same distance in order to be aligned. Thus, the control and monitoring of the system 240 can be more efficient. There are not two separate rolls to be managed at different dispensing rates, and there is no additional scanning to match the markings on two different rolls, when cutting or sealing in the present invention.

As such, the system 240 further comprises a lower turn bar 103 below the first roll 102 so as to conveying the bottom sheet material 140 in a second direction 96 orthogonal to the first direction 98, and an upper turn bar 101 above the first roll 102 so as to conveying the top sheet material 130 in a third direction 94 orthogonal to the first direction 98 and opposite and parallel to the second direction 96. There is a plurality of upper rollers 109 switching the top sheet material 130 between the third direction 94 and the second direction 96, and there is a plurality of lower rollers 107 switching the bottom sheet material 140 between the second direction 96 and the third direction 94. The system 240 sets the upper rollers 109 and the lower rollers 107 to match the distance traveled by the top sheet material 130 and the bottom sheet material 140, so that the markings and labels of each assembly 10 remain aligned.

There is a second roll 102 of foam material 160 mounted orthogonal to the first roll 100. The second roll 102 dispenses the foam material 160 in the third direction 94 along the system 240. The second roll 102 is mounted at one end of the system 240. FIGS. 7 and 10 show a foam cutter 105 aligned with the second roll 102 so as to cut the foam material 160 into a plurality of insert bodies 60 and a perforated foam material sheet 161. The foam material 160 matches the bottom sheet material 140 in the third direction 94 at the foam cutter 105. In some embodiments, the foam cuter is a die cutter but other known cutters are possible. The foam material 160 is above the bottom sheet material 140.

In some embodiments, there is a third roll 104 below the second roll 102 so as to store the perforated foam material sheet 161. The perforated foam material sheet 161 is a web material to be recovered so as to avoid affecting alignment of the other sheet materials 130, 140 and the insert bodies 60 cut from the foam material 160. FIGS. 7 and 10 show the perforated foam material 161 conveyed in the second direction 96 away from the plurality of insert bodies 60 and between the foam material 160 to be cut and the bottom sheet material 140. The foam material 160 and perforated foam material sheet 161 are isolated from the bottom sheet material 130 at the foam cutter 105.

There can also be a position scanner 111 positioned above the bottom sheet material 140 after the foam cutter 105. The position scanner 111 monitors alignment of the insert bodies 60. Each insert body 60 is aligned by being laid on the bottom sheet material 140 while matching the bottom sheet material 140 in the third direction 94. The insert bodies 60 pass the position scanner 111 so as to confirm alignment of each insert body 60 on the bottom sheet material 140. Each insert body 60 is removable adhered to the bottom sheet material 140, so each insert body 60 is able to move or shift. In some embodiments, static electricity or other removably adhering means is used to maintain alignment on the bottom sheet material 140.

FIGS. 7 and 10 also show a dispenser 106 having the chemical composition 200, 210, 220 stored within the dispenser 106. The chemical composition 200, 210, 220 is suitable to be stored and dispensed from the dispenser 106. The chemical composition 200, 210, 220 can be loaded and stored as cartridges or pumped to the dispenser 106 from a larger supply. The viscosity and activity of the chemical composition 200, 210, 220 is compatible with the dispenser 106 in the system 240. The dispenser 106 is positioned above each insert body 60 and the bottom sheet material 140 and after the foam cutter 105. The dispenser 106 move to match the bottom sheet material 140 in the third direction 94 so that the chemical composition 200, 210, 220 can be delivered or sprayed on the insert body 60, while moving across and along the bottom sheet material 140, which is also moving in the third direction 94. A set amount of the chemical composition 200, 210, 220 and a respective insert body 60 form an insert 50 for each insert body 60.

For some embodiments of FIGS. 7 and 10, the dispenser 106 includes a sprayer 113 so as to deliver the set amount of the chemical composition 200, 210, 220 corresponding to a single dose for each insert 50. The set amount is positioned on the applicator portion 64, and the set amount is divided between each cyclic group 66 of the applicator portion 64. The dispenser 106 is movable across the bottom sheet material 140 and each insert body 60 for a delivery time period. The delivery time period is the time needed to dispense the chemical composition 200, 210, 220 three times in FIGS. 1, 7 and 10. The delivery time period corresponds to a distance between the foam cutter 105 and a flatbed heat seal packager 108. The dispenser 106 is movable in the second direction 96 to align with another insert body 60 upstream toward the foam cutter 105, after reaching the flatbed heat seal packager 108. The dispenser 105 can spraying any pattern of chemical composition 200, 210, 220 as the same or different compositions. The dispenser 105 moves to spray on each insert body 60 and to match the movement of the bottom sheet material 140 as a conveyor belt.

Figure 11:
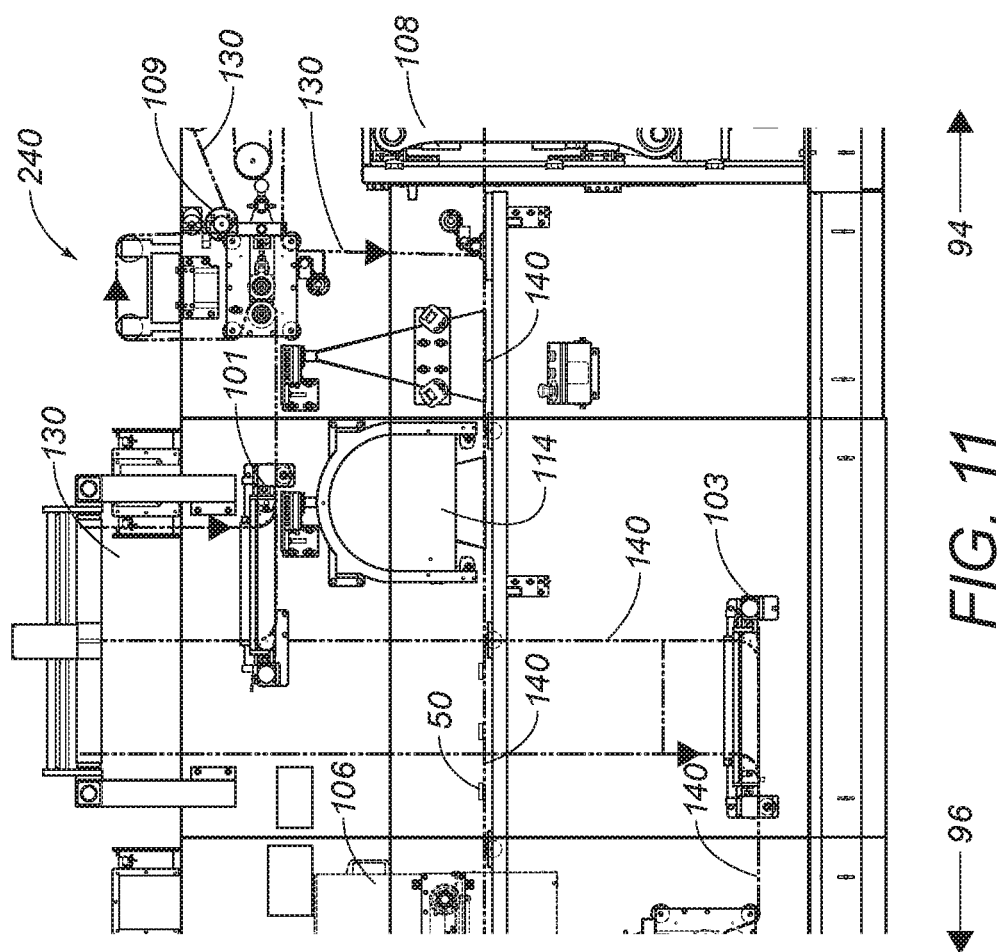
FIG. 11 is an enlarged side elevation view of another portion of a system to manufacture an assembly, according to an embodiment of the present invention.

As shown in FIGS. 7 and 11, the system 240 further comprises a first scanner 114. The inserts 50 now need to be checked so as to confirm alignment on the bottom sheet material 140, proper dispensing of the chemical composition 200, 210, 220, and alignment of the chemical composition 200, 210, 220 on the insert body 60. For each insert 50, the first scanner 114 is positioned away from the dispenser 106 and along the bottom sheet material 140 in the third direction 94. The first scanner 114 can be selected from a group consisting of a vision sensor, a splice sensor, and another sensor. FIG. 11 shows a vision sensor. As part of the web conversion again, the alignment of the insert 50 with chemical composition 200, 210, 220 needs confirmation because the bottom sheet material 140 is going to be cut later in the process. In some embodiments, there is a plurality of first scanners 114. More than one scanner can perform the monitoring of alignment, and any combination of a vision sensor, a splice sensor, and another sensor can be selected.

Figure 12:
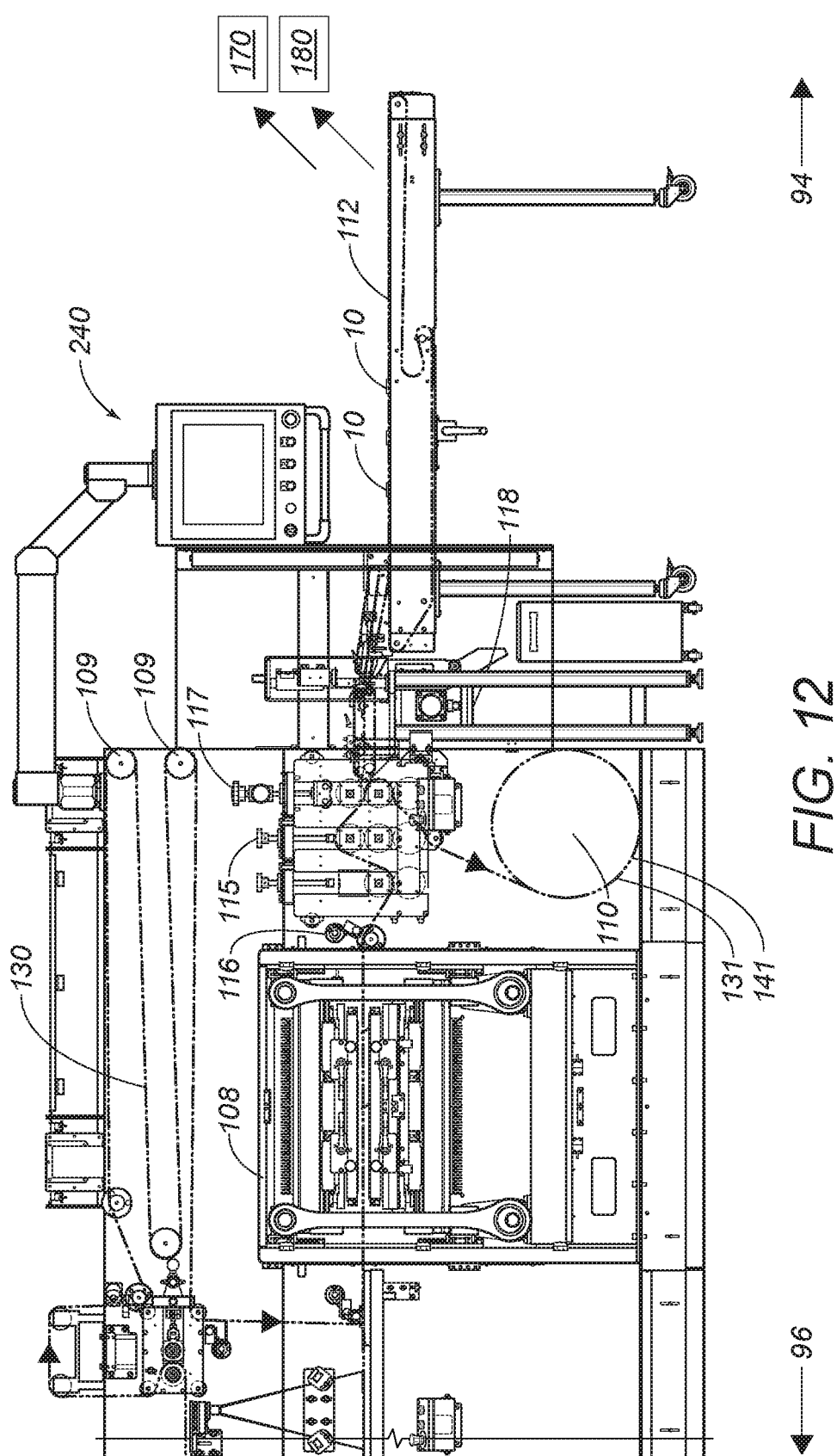
FIG. 12 is an enlarged side elevation view of still another portion of a system to manufacture an assembly, according to an embodiment of the present invention.

Embodiments of the system 240 are further shown in FIGS. 7 and 12 with the flatbed heat seal packager 108 positioned along the bottom sheet material 140 in the third direction 94 after the dispenser 106. The flatbed heat seal packager 108 is also movable in the third direction 94 and matches both the bottom sheet material 140 and the top sheet material 130 in the third direction 94. The upper turn bar 101 and the upper rollers 109 align the top sheet material 130 above the insert 50 and the bottom sheet material 140. The top sheet material 130 from the upper turn bar 101 to the flatbed heat seal packager 108 matches the bottom sheet material 140 from the lower turn bar 103 to the flatbed heat seal packager 108 in distance traveled so that the markings and labels on the wrapper material 120 remain aligned for each assembly 10. The flatbed heat seal packager 108 seals the top sheet 30 of the top sheet material 130 to a bottom sheet 40 of the bottom sheet material 140 around each insert 50 so as to form the border 22 along a perimeter of each insert 50. Each insert 50 is now positioned between the top sheet 30 and the bottom sheet 40, while the flatbed heat seal packager 108 matches the bottom sheet material 140 and the top sheet material 130 in the third direction 94. The border 22 is aligned with the applicator portion 64 to maintain the insert 50 in place within the border 22.

FIG. 12 shows the flatbed heat seal packager 108 as movable along the bottom sheet material 140 and the top sheet material 130 for a packaging time period. The packaging time period is the time to seal and form the border for each insert 50 in the flatbed heat seal packager 108. The packaging time period also corresponds to a distance traveled by the flatbed heat seal packager 108 between the dispenser 106 and a sheet cutter 117. The flatbed heat seal packager 108 moves back in the second direction 96 to align with another insert 50 upstream toward the dispenser 106, after reaching the sheet cutter 117 and completing the borders 22 on the inserts 50. The flatbed heat seal packager 108 moves in the third direction 94 and second direction 96.

As shown in FIGS. 7 and 12, the system 240 further comprises a second scanner 116 positioned between the flatbed heat seal packager 10 and the sheet cutter 117 in the third direction 94. The inserts 50 with borders 22 now need to be checked so as to confirm the seal and border 22 of the top sheet material 130 and the bottom sheet material 140. For each insert 50 with border 22, the second scanner 116 is positioned away from the flatbed heat seal packager 108 and along the bottom sheet material 140 in the third direction 94. The second scanner 116 can be selected from a group consisting of a photoelectric sensor, a vision sensor, a splice sensor, and another sensor. FIG. 12 shows a photoelectric sensor. As part of the web conversion, the seal of the insert 50 by the border 22 needs confirmation because the top sheet material 130 and the bottom sheet material 140 are going to be cut together next in the process. The second scanner 116 may also include a plurality of scanners in combination.

The embodiment of FIG. 12 shows a nip machine 115 between the flatbed heat seal packager 108 and the sheet cutter 117 in the third direction 94. Since each border 22 requires an incision 26 to form the tab 24 of the assembly 10, the nip machine 115 cuts the incision 26 within the border 22, before the borders 22 are cut from the top material sheet 130 and the bottom material sheet 140.

The system 240 further comprises the sheet cutter 117 positioned along the bottom sheet material 140 and the top sheet material 130 in the third direction 94 after the flatbed heat seal packager 108. Each border 22 is cut from the top sheet material 130 and the bottom sheet material 140 so as to form an assembly 10 from each border 22. The cutting also generates a perforated top sheet material 131, and a perforated bottom sheet material 141. Each assembly 10 now comprises a respective insert 50 and a wrapper 20 having the top sheet 30 from the top sheet material 130 and the bottom sheet 40 from the bottom sheet material 140. The assemblies 10 are conveyed to an outfeed conveyor 112 moving in the third direction 96 away from the sheet cutter 117.

FIGS. 7 and 12 also disclose the treatment of the web materials as the perforated top sheet material 131 and the perforated bottom sheet material 141. There can be a fourth roll 110 below the outfeed conveyor 112 so as to store the perforated top sheet material 131 and the perforated bottom sheet material 141 together. The perforated top sheet material 131 and the perforated bottom sheet material 141 are recovered for disposal, recycling, and to avoid hindering the top sheet material 130 and bottom sheet material 140 still being processed by the system 240. The perforated top sheet material 131 and the perforated bottom sheet material 141 are conveyed in the second direction 96 away from the outfeed conveyor 112 and below the outfeed conveyor 112.

Embodiments of the system 240 further include a packing means 170 or a sorting means 180 or both. The packing means 170 connects to the outfeed conveyor 112 for placing the assemblies 10 into boxes or sleeves for transport. The packing means 170 can be manual or any known automated machine, such as a collector and boxing machine. Alternatively, there can be a sorting means 180 separate or cooperative with the packing means 170. The sorting means 180 can divide and separate the assemblies 10 from the outfeed conveyor 112 into groups. The groups may be associated with packaging for the packing means 170, such as packing a group of twelve assemblies 10 in one box. The groups may also be associated with different chemical compositions 200, 210, 220. The scanners 111, 114, 116 have detected the contents of the assemblies 10, and the markings and labels on the top sheet 30 and the bottom sheet 40 are known. Thus, the sorting means 180 can be manual or any known automated machine, such as a swivel arm and different sleeves for grouping.

FIGS. 7 and 12 also show embodiments with a reject conveyer 118. The reject conveyer 118 is positioned after the sheet cutter 117 in the third direction 94. The scanners 111, 114, 116 have been detecting and monitoring for any errors in the manufacturing process. The system 240 maintains and records the position of each insert body 60, corresponding insert 50, and corresponding assembly 10. So, any error or anomaly detected as an insert body 60, an insert 50, or assembly 10 can be tracked as a tagged assembly. When that tagged assembly reaches the reject conveyer 118, the tagged assembly is separated from the other assemblies 10. The system 240 can detect errors and remove assemblies that do not meet quality control requirements. The coordination of the components of the system 240 allow for accurate tracking and the possible use of a reject conveyor 118 as automated quality control.

Method for Manufacturing a Disposable Single use Applicator Assembly with a Chemical Composition Embodiments of the present invention include the method of manufacturing with the system 240 for the disposable single use applicator assembly 10 with a chemical composition 200, 210, 220. The method tracks closely to the system 240. As shown in FIGS. 7-12, the method of manufacturing, comprises the steps of: mounting a first roll 100 of wrapper material 120, dispensing the wrapper material in a first direction 98, splitting the wrapper material into a top sheet material 130 and a bottom sheet material 140, conveying the bottom sheet material 140 in a second direction 96 orthogonal to the first direction 98 by a lower turn bar 103, and conveying the top sheet material 130 in a third direction 94 orthogonal to the first direction 98 and opposite and parallel to the second direction 96 by an upper turn bar 101. The top sheet material 130 switches between the third direction 94 and the second direction 96 by a plurality of upper rollers 109, and the bottom sheet material 140 switches between the second direction 96 and the third direction 94 by a plurality of lower rollers 107. The method matches the top sheet material 130 and the bottom sheet material 140 from the wrapper material 120 orthogonal to components of the system 240, while maintaining the alignment of markings and labels on the top sheet material 130 and the bottom sheet material 140.

Next, the method mounts a second roll 102 of foam material 160 orthogonal to the first roll 100, and dispenses the foam material 160 in the third direction 94. The foam material 160 matches the bottom sheet material 140 in the third direction 94 at a foam cutter 105 aligned with the second roll 102. The foam material 160 runs above the bottom sheet material 140. When the foam material 160 is cut into a plurality of insert bodies 60 and a perforated foam material sheet 161 with the foam cutter 105, the insert bodies 60 are laid on the bottom sheet material 140 in motion in the third direction 94. The method aligns each insert body 60 on the bottom sheet material while matching the bottom sheet material in the third direction.

In this sequence, the system 240 has stored a chemical composition 200, 210, 220 in a dispenser 106 positioned after the step of cutting the foam material 160. The dispenser 106 is positioned above each insert body 60 and the bottom sheet material 140 after the foam cutter. The method includes dispensing the chemical composition 200, 210, 220 from the dispenser 106 on each insert body 60 while matching the bottom sheet material 140 in the third direction 94, so as to form an insert 50, corresponding to each insert body 60. A set amount of the chemical composition 200, 210, 220 corresponding to a single dose is delivered for each insert 50, and the dispenser 106 matches the bottom sheet material 140 in the third direction 94.

Embodiments of the step of matching the dispenser 106 include moving the dispenser 106 across the bottom sheet material 140 and over each insert body 60 for a delivery time period. The delivery time period corresponds to a duration of time for the step of dispensing to each insert body 60 so as to form each insert 50, and aligning the dispenser 106 with another insert body 60 upstream toward the foam cutter 105 by moving in the second direction 94, after the delivery time period of the step of dispensing. Any pattern by spraying on the insert body 60 is performed while matching the dispenser 106 to the bottom sheet material 140 in the third direction 94.

The method further includes curing the chemical composition 200, 210, 220 on the foam material 160 of the insert body 60 with the foam material 160 being comprised of a foam composition 230. The chemical composition 200, 210, 220 and the foam composition 230 are cooperative to complete the step of curing within the time between the dispenser 106 and the flatbed heat seal packager 108 and within the distance between the dispenser 106 and the flatbed heat seal packager 108. Each insert 50 on the bottom sheet material 140 is conveyed for a conveyer time period away from the dispenser 106, the conveyor time period corresponding to a duration of time for the step of curing.

Next, a top sheet 30 of the top sheet material 130 is sealed to a bottom sheet 40 of the bottom sheet material 140 around each insert 50 so as to form a border 22 along a perimeter of each insert 50 with the flatbed heat seal packager 108. Each insert 50 is positioned between the top sheet 30 and the bottom sheet 40, while the flatbed heat seal packager 108 matches and aligns with the bottom sheet material 140 and now the top sheet material 130 in the third direction 94 The flatbed heat seal packager is 108 positioned along the bottom sheet material 140 in the third direction 94 after the dispenser, and move in the third direction 94 according to both the bottom sheet material 140, and the top sheet material 130 in the third direction 94 during the step of sealing. The sealing is usually performed in groups of inserts 50, so more than one border 22 is formed. A group of borders 22 are formed to seal a group of inserts 50 within the flatbed heat seal packager 108.

The upper turn bar 101 and the upper rollers 109 align the top sheet material 130 above the insert 50 and the bottom sheet material 140, and the top sheet material 130 from the upper turn bar 101 to the flatbed heat seal packager 108 matches the bottom sheet material 140 from the lower turn bar 103 to the flatbed heat seal packager 108. The markings and labels on the wrapper material 120 remain aligned.

Additionally, the flatbed heat seal packager 108 matches the top sheet material 130 and the bottom sheet material 140 in the third direction 94 during the step of sealing. In particular embodiments, the step of matching the flatbed heat seal packager 108 includes moving the flatbed heat seal packager 108 for a packaging time period. The packaging time period corresponds to a duration of time for the step of sealing for each border 22 and to a distance between the dispenser 106 and the sheet cutter 117. Eventually, the flatbed heat seal packager 108 separates from the top sheet material 130 and the bottom sheet material 140. Then, the flatbed heat seal packager 108 is moved back in the second direction 96 toward the dispenser 106 to align with another insert 50 upstream from the sheet cutter 117.

The method further includes cutting each border 22 from the top sheet material 130 and the bottom sheet material 140 with a sheet cutter 117 so as to form an assembly 10 for each border 22, a perforated top sheet material 131, and a perforated bottom sheet material 141. An outfeed conveyor 112 collects each assembly 10 and moves the assemblies 10 in the third direction 94 away from the sheet cutter 117.

Embodiments of the method include additional steps, according to components in the system 240.

With a third roll 104 below the second roll 102, the method including recovering the perforated foam material sheet 161. As part of the web conversion process, the perforated foam material sheet 161 should be addressed to maintain alignment of the bottom sheet material 140 and foam material 160 currently in the method. This embodiment includes conveying the perforated foam material 161 in the second direction 96 away from the plurality of insert bodies 60 and between the foam material 160 and the bottom sheet material 140. The perforated foam material sheet 161 is stored on the third roll 104.

When the system 240 has an alignment means, the step of aligning the insert body 60 can further include laying each insert body 60 on the bottom sheet material 140 while conveying the bottom sheet material 140 in the third direction 94, and adhering each insert body 60 to the bottom sheet material 140. An alignment means may be a static electricity generator so that insert body 60 is removable adhered by static electric. Other alignment means, such as air puffs or adhesives are also possible.

Embodiments of the method include detecting each insert body 60 by a position scanner 111 so as to confirm alignment on the bottom sheet material 140. A misaligned insert body can be identified and tracked through the system 240. The system 240 can control the dispenser 106 to not deliver the set amount to the misaligned insert body or a reject conveyor 118 can discard the bad assembly corresponding to the misaligned insert body.

FIGS. 7 and 10 also show a sprayer 113 as part of the dispenser 106. The method includes spraying the set amount or a plurality of set amounts of the chemical composition 200, 210, 220. Any pattern of chemical compositions 200, 210, 220 can be sprayed, even with the chemical compositions 200, 210, 220 being the same or different or any combination thereof.

Embodiments of the method include another step in the web conversion process of the system 240. The method can include detecting each insert with a first scanner 114 so as to confirm alignment on the bottom sheet material 140, application or presence of the chemical composition 200, 210, 220 on the insert body 60, and alignment of the chemical composition 200, 210, 220 on the insert body 60, after the step of dispensing. The first scanner 114 can be selected from a group comprising: a vision sensor, a splice sensor, and another sensor. The first scanner 114 identifies a misapplied insert, just as the position sensor 111 identifies a misaligned insert body. The misapplied insert can be identified and tracked through the system 240. The system 240 can control the flatbed heat seal packager 108 to not seal a border or the reject conveyor 118 can discard the bad assembly corresponding to the misapplied insert. The method includes detecting with more than one first scanner 114 also.

Embodiments of the method include still another step in the web conversion process of the system 240. The method can include detecting each insert with a second scanner 116 so as to confirm the border 22 of each insert 50 before cutting. The second scanner 116 can be selected from a group comprising: a photoelectric sensor, a vision sensor, a splice sensor, and another sensor. FIG. 12 shows the second scanner 116 as a photoelectric sensor. The second scanner 116 identifies a mis-sealed border, just as the position sensor 111 identifies a misaligned insert body. The mis-sealed border can be identified and tracked through the system 240. The system 240 can control the sheet cutter 117 to not cut or the reject conveyor 118 can discard the bad assembly corresponding to the mis-sealed border. The method includes detecting with more than one second scanner 116 also.

When the system 240 has a nip machine 115, the method can include an embodiment with the step of cutting an incision 26 in each border 22 so as to form a tab 24 for each border 22. The incision 26 ca be within the border 22 so that the insert 50 remains sealed within the border 22, until the tab 24 breaches the border 22 and separates the top sheet 30 and the bottom sheet 40. In this embodiment, the step of cutting the incision 26 is before the step of cutting each border 22.

FIGS. 7 and 12 also show embodiments of the system 240 with a fourth roll 110 below the outfeed conveyor 112. The corresponding embodiment of the method includes recovering the perforated top sheet material 131 and the perforated bottom sheet material 141 together. As another part of the web conversion process, the perforated top sheet material 131 and the perforated bottom sheet material 141 are addressed together to maintain alignment of the top sheet material 130 and the bottom sheet material 140. This embodiment includes conveying the perforated top sheet material 131 and the perforated bottom sheet material 141 in the second direction 96 away from the outfeed conveyor 112. The perforated top sheet material 131 and the perforated bottom sheet material 141 is stored on the fourth roll 110.

Additional embodiments of the method include the system 240 with a packing means 170 or a sorting means 180 or both. The method can include the step of packing assemblies 10 from the outfeed conveyor 112. The packing means 170 can be connected to the outfeed conveyor 112 so that the assemblies 10 are placed into boxes or sleeves for transport manually or by an automated machine. The method can also include sorting assemblies 10 from the outfeed conveyor 112 before the step of packing assemblies 10. The method divides and separates the assemblies 10 from the outfeed conveyor 112 into groups. The groups may be associated with packaging for the packing means 170, such as packing a group of twelve assemblies 10 in one box. The groups may also be associated with different chemical compositions 200, 210, 220. The scanners 111, 114, 116 have detected the contents of the assemblies 10, and the markings and labels on the top sheet 30 and the bottom sheet 40 are known. Thus, the sorting means 180 can be manual or any known automated machine, such as a swivel arm and different sleeves for grouping.

FIGS. 7 and 12 also show embodiments of the method with a reject conveyer 118. The reject conveyer 118 is positioned after the sheet cutter 117 in the third direction 94. The method includes the step of rejecting assemblies identified as bad assemblies from any scanner 111, 114, 116 with the reject conveyor 118. After the steps of detecting and monitoring for any errors in the manufacturing process with the sensors or scanners 111, 114, 116, the method includes maintaining and recording the position of each insert body 60, corresponding insert 50, and corresponding assembly 10 in the system 240. The method further includes tracking any error or anomaly detected as an insert body 60, an insert 50, or assembly 10 as a tagged assembly. When that tagged assembly reaches the reject conveyor 118, the method separates the tagged assembly from the other assemblies 10. The method of using the system 240 detects errors and removes assemblies that do not meet quality control requirements. The method coordinates components of the system 240 for accurate tracking and rejecting tagged assemblies with a reject conveyor 118 as an automated quality control process.

Additional Relationships

The assembly 10 as an embodiment of the present invention further describes the method of manufacture. In this variation, the step of cutting the foam material 160 into the plurality of insert bodies 60 includes forming the insert body 60 of the assembly 10. Thus, the step of cutting can further includes forming the insert body 60 having rotational symmetry of at least four cyclic groups 66, wherein the handle portion corresponds to only one cyclic group 66. Also, the step of dispensing can further include positioning the set amount on the applicator portion 64 and dividing the set amount between each cyclic group 66. The same variations to the method apply to the chemical composition 200, 210, 220 being a cosmetic in the assembly 10. The step of cutting can further include forming the insert body 60 having rotational symmetry of at least four cyclic groups 66, wherein the handle portion corresponds to only one cyclic group 66. Also, the step of dispensing can further include positioning the set amount on the applicator portion 64 and dividing the set amount between each cyclic group 66 for a single application of a cosmetic. With the embodiment of the assembly 10 with the chemical composition 200, 210, 220 as a plurality of different chemical compositions 200, 210, 220, the step of dispensing can further include positioning each set amount on the applicator portion 64 and positioning each set amount on a respective cyclic group 66 separate from other cosmetics and another cyclic group 66.

The chemical composition 200, 210, 220 as an embodiment of the present invention further describes the assembly 10. In these embodiments of the assembly 10, the insert 50 comprises the set amount of the chemical composition 200, 210, 220 as claimed for a single dose or a single application, when the chemical composition is a cosmetic. So, the embodiments of the assembly 10 now include a particular chemical composition 200, 210, 220 on the insert body 60 having rotational symmetry of at least four cyclic groups 66, wherein the handle portion corresponds to only one cyclic group 66. The set amount of the particular chemical composition 200, 210, 220 is positioned on the applicator portion 64 and divided between each cyclic group 66 of the applicator portion 64.

In other embodiments of the assembly 10, there is a plurality of set amounts of chemical compositions 200, 210, 220 on the insert body 60, when the plurality of set amounts is required for a single dose or single application. Each set amount is positioned on the applicator portion 64 is positioned, and each set amount is positioned on a respective cyclic group 66 separate from other cosmetics and another cyclic group 66.

The chemical composition 200, 210, 220 as an embodiment of the present invention further describes the method to manufacture the assembly 10 as well. The step of storing, the step of dispensing, and the step of curing are further modified by the chemical composition 200, 210, 220 disclosed as an embodiment of the invention. The step of storing is modified to include the particular chemical composition 200, 210, 220 claimed, and the step of dispensing is modified to include the particular chemical composition 200, 210, 220. The step of curing can also be described as an alternate embodiment of the method to manufacture. The step of curing can include adhering the chemical composition 200, 210, 220 to the foam composition 230 or drying the chemical composition 200, 210, 220 on the foam composition 230 or both.

Between the step of dispensing the chemical composition 200, 210, 220 and the step of sealing the top sheet 30, the chemical composition 200, 210 220 has a rate of evaporation so as to dry between the step of dispensing and the step of sealing the top sheet 30. The chemical composition 200, 210, 220 is sealed in an active state for use when the assembly 10 is opened later. An amount of moisture is evaporated during this method so that there is the active state, when the assembly 10 is opened later.

In the method to manufacture the assembly 10 with the chemical composition 200, 210, 220, chemical composition 200, 210, 220 has a first amount of adhesion in the step of adhering and a second amount of adhesion before the step of sealing the top sheet 30. The second amount of adhesion is less than the first amount of adhesion. Also, the conveyor time period of the step of conveying each insert 50 on the bottom sheet material 140 matches the step of drying the chemical composition 200, 210, 220.

The foam composition 230 as an embodiment of the present invention further describes both the assembly 10 and the method to manufacture the assembly 10.

In these embodiments of the assembly 10, the insert 50 comprises the set amount of the chemical composition 200, 210, 220 on the insert body 60 as claimed for a single dose or a single application, when the chemical composition is a cosmetic. So, the embodiments of the assembly 10 now include a particular chemical composition 200, 210, 220 on the insert body 60 with the foam composition 230 as claimed. The insert body 60 still has rotational symmetry of at least four cyclic groups 66, wherein the handle portion corresponds to only one cyclic group 66. The set amount of the particular chemical composition 200, 210, 220 is still positioned on the applicator portion 64 and divided between each cyclic group 66 of the applicator portion 64, wherein the applicator portion 64 is made of the foam composition 230 as claimed.

In other embodiments of the assembly 10, there is a plurality of set amounts of chemical compositions 200, 210, 220 on the insert body 60 of the claimed foam composition 230, when the plurality of set amounts is required for a single dose or single application. Each set amount is positioned on the applicator portion 64 is positioned, and each set amount is positioned on a respective cyclic group 66 separate from other cosmetics and another cyclic group 66, wherein the applicator portion 64 is made of the foam composition 230 as claimed.

The foam composition 230 as an embodiment of the present invention further describes the method to manufacture the assembly 10 similar to how the chemical composition 200, 210, 220 described the method. The step of dispensing and the step of curing are further modified by the foam composition 230 interacting with the chemical composition 200, 210, 220 disclosed as an embodiment of the invention. The step of dispensing is modified to include the particular chemical composition 200, 210, 220 on the insert body 60 of the foam composition 230 as claimed. The step of curing can also be described as an alternate embodiment of the method to manufacture. The step of curing can include adhering the chemical composition 200, 210, 220 to the foam composition 230 or drying the chemical composition 200, 210, 220 on the foam composition 230 or both.

Between the step of dispensing the chemical composition 200, 210, 220 and the step of sealing the top sheet 30, the chemical composition 200, 210 220 has a rate of evaporation so as to dry on the insert body 60 of the foam composition 230 between the step of dispensing and the step of sealing the top sheet 30. The chemical composition 200, 210, 220 is sealed in an active state for use when the assembly 10 is opened later. An amount of moisture is evaporated during this method so that there is the active state, when the assembly 10 is opened later.

In the method to manufacture the assembly 10 with the chemical composition 200, 210, 220 on the insert body of the foam composition 230, chemical composition 200, 210, 220 has a first amount of adhesion in the step of adhering and a second amount of adhesion before the step of sealing the top sheet 30. The second amount of adhesion is less than the first amount of adhesion. Also, the conveyor time period of the step of conveying each insert 50 on the bottom sheet material 140 matches the step of drying the chemical composition 200, 210, 220.

The present invention delivers a cosmetic, health or hygiene chemical composition in an active state, after being packaged and stored in a disposable single use assembly. The assembly itself is portable and convenient for storing in bulk or transporting individually in a purse or pocket. The assembly aligns the applicator as an insert body within the wrapper, so that the applicator portion with the chemical composition is stabilized. The border of the wrapper holds the insert in position within the wrapper so that the chemical composition is not spread all over the insert. The handle portion remains isolated and clean. When the assembly is opened, the handle portion is available for use, without getting the chemical composition on fingers or hands.

The relationship between the insert and the wrapper provides a cosmetic, health or hygiene chemical composition on an applicator for delivery in an active state to the user. The active state is preserved, even after the manufacturing process and storage in the assembly. The active state is also preserved for each chemical composition, when there is more than one chemical composition on the insert, such as an assembly with different cosmetics on each insert. The insert, border, and wrapper can also preserve the active state of more than one cosmetic in the same assembly. The applicator assembly of the present invention stores and carries cosmetics in a simple, easy, and inexpensive container.

The present invention includes the chemical composition compatible with the assembly. A set amount of the chemical composition is stored in each assembly, and the chemical composition can be a cosmetic or several different cosmetics. The set amount corresponds to a single dose, or a single application for when the chemical composition is a cosmetic. The chemical composition is compatible with the manufacturing process of the assembly. The active state of the chemical composition is maintained during the step of dispensing the set amounts on each insert and the step of curing on each insert before the step of sealing. Any drying or degradation of the chemical composition is coordinated with the manufacturing process. Additionally, the chemical composition is compatible with the assembly and the relationship between the insert, border, and wrapper. The chemical composition can be applied to the insert as required to maintain the alignment within the wrapper to preserve the active state.

The present invention includes the foam composition. The insert body is made of the foam composition. The insert body is important to hold the chemical composition within the assembly, and the insert body must also be compatible with the manufacturing process so that the chemical composition on the insert body can maintain an active state in the assembly. The assembly may be stored and transported for an extended period of time, such as months and maybe years. The foam composition must remain durable, so that the insert can administer the chemical composition, even after such time has passed. The foam composition must be compatible with use as an insert body to administer the chemical composition, in addition to maintaining the active state of the chemical composition in the manufacturing process and keeping alignment within the assembly.

The active state of the chemical composition is further maintained during the step of dispensing the set amounts on the foam composition of each insert and the step of curing on the foam composition of each insert before the step of sealing. The chemical composition must be able to adhere to the foam composition, in addition to maintaining an active state. Any drying or degradation of the chemical composition on the foam composition is also coordinated with the manufacturing process. Additionally, the foam composition is compatible with the assembly and the relationship between the insert, border, and wrapper. The foam composition supports the chemical composition in place and has rigidity to maintain the alignment within the wrapper to preserve the active state. Furthermore, after extended time, the foam composition is resilient to be used to administer the chemical composition, whenever the assembly is opened for use.

The present invention includes the system and method to manufacture the assembly. The process as a web conversion process must account for the alignment and tracking of web materials. The system must set the components in position to complete the sequence. In the present invention, there are additional considerations for the position to other components, sequence, timing, and distance for the particular chemical composition and foam composition for the assembly. The method includes an orthogonal dispensing of the wrapper material and split into two directions of the top sheet material and the bottom sheet material. The system includes the turn bars and rollers to accomplish this sequence. The top sheet material is matched back to the bottom sheet material at the sealing stage. Additionally, the step of dispensing the chemical composition is matched in the third direction, according to time to dispense and distance to the flatbed heat seal packager. The sequence for the drying and curing of the chemical composition to remain in the active state is compatible for the chemical composition and foam composition as claimed. The time between dispensing and sealing can deliver the cosmetic, health, or hygiene chemical composition in an active state to the user. Furthermore, the placement of the foam cutter and the sheet cutter maintains alignment of the insert within the wrapper.

The embodiments of the present invention provide an applicator assembly for disposable single use. In order to maintain the active state of the chemical composition in the assembly, the present invention includes the alignment of components of the assembly and the manufacturing process for the assembly. Additionally, the chemical composition and foam composition are embodiments for the system and method of manufacturing the assembly.

The foregoing disclosure and description of the invention is illustrative and explanatory thereof. Various changes in the details of the illustrated structures, construction and method can be made without departing from the true spirit of the invention.

I claim:

1. An assembly for storing and transporting, said assembly comprising:
   a wrapper having a top sheet and a bottom sheet, said top sheet being sealed to said bottom sheet so as to form a border along a perimeter of said top sheet and said bottom sheet; and
   an insert having a top surface and a bottom surface, said insert being comprised of an insert body with a handle portion and an applicator portion,
   wherein said insert body is positioned between said top sheet and said bottom sheet, and
   wherein said border aligns with said applicator portion only so as to maintain said insert in place within said wrapper,
   wherein said insert further comprises:
   a set amount of a chemical composition being comprised of a cosmetic corresponding to a single application, and wherein said set amount is positioned on said applicator portion,
   wherein said insert body has rotational symmetry having at least four cyclic groups,
   wherein said handle portion corresponds to only one cyclic group,
   wherein said border is comprised of an applicator border segment and a handle border segment,
   wherein said set amount is divided between each cyclic group of said applicator portion, each cyclic group of said applicator portion having a respective set amount portion,
   wherein said applicator border segment is aligned with the cyclic groups corresponding to said applicator portion and said set amount on at least one cyclic group corresponding to said application portion and directly opposite said handle portion, and
   wherein said handle border segment extends across said insert body adjacent to said handle portion.

2. The assembly, according to claim 1, further comprising:
   a tab being comprised of an incision in said border, said incision being within said border, said insert being sealed within said border until said tab separates said top sheet and said bottom sheet.

3. The assembly, according to claim 1, said border being aligned with the cyclic groups corresponding to said application portion and directly opposite said handle portion.

4. The assembly, according to claim 1, said border being aligned with at least one cyclic group corresponding to said application portion and directly opposite said handle portion and parts of cyclic groups corresponding to said application portion, wherein said border is on a side of said insert body opposite to said handle portion.

5. The assembly, according to claim 1, wherein said handle portion further comprises a gripping means.

6. The assembly, according to claim 1, wherein said insert further comprises:
   a plurality of set amounts of a plurality of chemical compositions corresponding to a plurality of cosmetics for a single application.

7. The assembly, according to claim 6,
   wherein said insert body has rotational symmetry having at least four cyclic groups, and wherein said handle portion corresponds to only one cyclic group, and
   wherein each set amount is positioned on a corresponding cyclic group of said applicator portion, each cosmetic being positioned on a respective cyclic group of said applicator portion separate from other cosmetics.

* * * * *